United States Patent [19]

Sick

[11] 4,032,236
[45] June 28, 1977

[54] OPTICAL MULTIPLE-REFLECTION ARRANGEMENT

[75] Inventor: Erwin Sick, Icking, Germany

[73] Assignee: Erwin Sick Optik-Elektronik, Waldkirch, Germany

[22] Filed: Jan. 28, 1976

[21] Appl. No.: 653,152

[30] Foreign Application Priority Data

Feb. 28, 1975 Germany .................. 2508860

[52] U.S. Cl. .................................... 356/201
[51] Int. Cl.² ................................ G01N 21/22
[58] Field of Search ................ 356/201, 207

[56] References Cited

UNITED STATES PATENTS

| | | | |
|---|---|---|---|
| 3,617,756 | 11/1971 | Sick | 356/207 |
| 3,857,641 | 12/1974 | Gass | 356/207 |
| 3,860,818 | 1/1975 | Stalder et al. | 356/201 |
| 3,885,162 | 5/1975 | Geertz | 356/207 |

FOREIGN PATENTS OR APPLICATIONS 617,416  2/1949  United Kingdom .............. 356/120

Primary Examiner—John K. Corbin
Assistant Examiner—R. A. Rosenberger

[57] ABSTRACT

Optical multiple-reflection arrangement comprising a light source, a lens separated from the source by its focal length in front of a retroreflector which returns a laterally offset beam, deflection means to displace the reflected image to one side of the source, and a second retroreflector near the image, whereby the measurement path between the retroreflectors is traversed at least four times by a beam from the source.

41 Claims, 12 Drawing Figures

OPTICAL MULTIPLE-REFLECTION ARRANGEMENT

The invention relates to an optical multiple-reflection arrangement having reflecton devices at both ends of a measurement path and having a light source or an image of a light source at one end of the measurement path, the light source and the reflection devices being so contructed and arranged that a light beam starting from the light source passes at least four times through the measurement path before it passes out of the latter.

Optical multiple reflection arrangements of this kind are used where long measurement paths are necessary, for example in order to obtain a distinct reception signal. By multiple reflection along the measurement path the latter can thus be substantially shortened, depending on the number of to-and-fro reflections effected. Examples of application are visibility measuring instruments on airfields and motorways, in which a light transmitter transmits a light beam over a distance of 10 or 30 meters to a reflector, which is preferably of retroreflecting material and which guides the light beam back in itself to the transmitter. Beam splitting is effected in the transmitter, and the reception light beam is directed onto a photo-receiver. The latter produces an electric signal the amplitude of which varies in dependence on the visibility (from more or less clear visibility, to fog). An electronic evaluation device forms from this signal an indication which can be expressed directly on a visibility scale. Another application is for exhaust gas density measuring instruments in tunnels, where the measurement path should, for example, extend over 100 meters. Finally, in this connection mention should also be made of smoke density measuring instruments disposed in chimneys, where the measurement path is limited to the diameter of the chimney.

Although optical multiple-reflection arrangements are of interest for the multiplication of the measurement path in a small space, the adjustment of the transmitter and receiver on the one hand and the reflection device on the other hand is problemmatical. The transmitter and receiver arrangement and the reflection device must be absolutely accurately aligned with respect to one another, in which connection a particular problem arises in completely maintaining over a long period of time an accurate adjustment once it has been achieved. Particularly in the case of smoke density measuring instruments, were continuous temperature fluctuations occur, this is extremely difficult.

It is therefore an object of the invention to provide an optical multiple-reflection arrangement of the kind first mentioned above, in which the light is transmitted and received from one side of the measurement and in which a reflection device, which need be only coarsely adjusted in relation to the transmitter-receiver, is disposed on the opposite side of the measurement path to that where the transmitter-receiver is disposed, and wherein certain variations of the adjustment during operation can be tolerated without the position and intensity of the reception light beam in the transmitter-receiver being influenced to such an extent as to impair the accuracy of measurement.

In order to solve this problem the invention provides for the reflection device disposed at the end of the measurement path remote from the light source to comprise a lens having a focal length equal to the distance from the light source, behind this lens a retroreflecting element which reflects an incoming light beam in the same direcion but offset laterally, and light beam deflection means which impart to the incoming and/or outgoing beams of the retroreflecting element a deflection such that the image made of the light source by the reflection device lies at the side of the light source, and that a second reflection device provided is a retroreflector disposed behind the image made of the light source by the first reflection device. On the side where the first reflection device is disposed there is therefore provided a single retroreflecting element which is preferably overshot by the light beam falling on it, so that as a whole neither a certain tipping of the reflection device nor lateral displacements bring about any change at the reception site or in the intensity of reception in the transmitter-receiver. It should be pointed out that the light source is preferably a slit illuminated by a lamp, a laser, or the like. However, in order to simplify the terminology used in this description the term "light source" will always be used even in the case of a simple illuminated slit or the like.

Whereas with a reflection device remote from the light source it is required that in addition to reflection in itself the beam should undergo lateral displacement, in the case of a retroreflector disposed by the light source it is required that the retro-reflector should reflect in the same direction the light falling on it.

In a first embodiment the beam deflection means consists of an optical wedge occupying one half of the beam path. The beam deflection means may however also consist of two optical wedges, disposed one in each half of the beam path. A particularly preferred embodiment is characterized in that the beam deflection means are formed by two half-lenses whose optical axes are spaced apart from one another in the direction of the offsetting of the light source. The optical axes of the half-lenses are offset in relation to one another to the extent necessary to project the image of the light source to the side of the latter.

Finally, the beam deflection means may also be formed by grinding one half of the lens or of the retroreflecting element so as to form a deviation from the normal shape. The only important point is that the image of the light source on the transmitter-receiver side should fall on the retroreflector to the side of the light source itself.

In the embodiment utilising half-lenses, it is expedient for the latter to be plano convex and to have their plane surface cemented on the likewise plane inlet surface of the retroreflecting element. A particularly compact unit not liable to shift is thereby formed.

The distance between the half-lenses is however variable, particularly for test purposes.

A triple mirror is used with particular advantage for the retroreflecting element.

The first reflection device preferably projects the image of the light source so that it directly adjoins the light source itself. Not only is optimum use thus made of the available space, but the size of the optical parts used is also reduced to a minimum.

In a first embodiment the retroreflector forming the second reflection device effects only a reversal of the beam without offsetting it. In this embodiment a four-fold passage of the light beam through the measurement path can be achieved.

In the simplest case the retroreflector consists of finely divided retroreflecting material, such as for example "Scotchlite".

The retroreflector may however also be a roof prism whose roof edge is situated in the middle of the image of the light source. In order to eliminate a certain sensitivity of height adjustment in this embodiment, the retroreflector is preferably a triple mirror, or better still, a Beck prism whose apex is situated in the middle of the light source image. A Beck prism is practically a disc-shaped portion of a triple mirror. The Beck prism is thus particularly suitable when working with an illuminated slit because the slit surface can be imaged in the base surface of the Beck prism. The base of the prism of triple mirror is advantageously equal in size to the image of the light source.

An embodiment which permits substantially more to-and-fro reflections is characterized in that the retroreflector forming the second reflection device effects a reversal of the beam with lateral offsetting to the extent of at least the size of the image of the light source. In this manner at least a sixfold passage of the light beam through the measurement path can be achieved.

In a first embodiment the retroreflector is once again a roof prism and the image of the light source is projected onto the half of this prism which faces the light source. In this embodiment, however, it is preferable for the retroreflector to be a triple mirror or better still a Beck prism. In contrast to the embodiment first described, the lateral offsetting is achieved by projecting the image of the light source not centrally onto the retroreflector but with lateral offsetting. In the preferred case of the use of a Beck prism the slit image expediently occupies exactly one half of the base surface. On the other half of the base surface the light then passes out accordingly.

In this embodiment also the retroreflector preferably directly adjoins the light source.

Another advantageous embodiment is characterized by the provision on the optical axis, in front of the retroreflector, of another lens whose focal length is equal to the distance from the first reflection device. The purpose of this measure is to ensure that all the light passing out of one half of the first reflection device will enter this half again. This is of importance because the light beams entering different halves of the reflection device are differently deflected. According to the invention, therefore, light beams should be clearly allocated to the respective halves of the reflection device.

The number of reflections within the measurement path can be increased by disposing a plurality of retroreflectors directly side by side. Each additional retroreflector increases the number of passages by four.

It should however be pointed out that the edge of the additional lens need extend only to the outer edge of the last retroreflector, so that the outgoing light beam goes past the lens.

In all embodiments the retroreflectors may be provided symmetrically on both sides of the light source, because the deflection of the light beams entering the entrance pupil or exit pupil of the first reflection device from the light source is effected entirely symmetrically.

According to another embodiment, when a retroreflector is used which reverses the beam and effects lateral offsetting in the directon of the light source, the lateral offsetting may amount to twice the size of the light source, the retroreflector preferably being a flattened roof prism in this case.

The flattened middle portion and the two lateral inclined portions of the roof prism are in this case expediently of the same size as the light source, while the centre of the roof prism lies in the optical axis. A fourfold passage is achieved with an arrangement of this kind. As compared with the embodiment first mentioned the advantage is gained that after the fourfold passage the light does not pass out of the measurement path at the site of the light source, but laterally offset thereto.

The use of an illuminated slit as light source is particularly convenient because a Beck prism can be disposed close to the slit.

A particularly suitable device for illuminating the slit is one in which the slit is illuminated by the slit of an inclined slit mirror and the side portions of the slit mirror receive the light reflected past the Beck prism or Beck prisms and guide it onto a photoreceiver. The advantage is thus gained that a partially transmitting mirror, which always entails losses of light, need not be used. As the result of the arrangement of the invention the light losses in the reception of the measurement beam are therefore substantially reduced.

Furthermore, the practical embodiment defined above makes it possible for a reference light beam from the main light source to be guided onto the photoreceiver through the slot alternately with the light from the measurement path.

The invention is described below by way of example and with reference to the drawings, in which.

Figure 1:
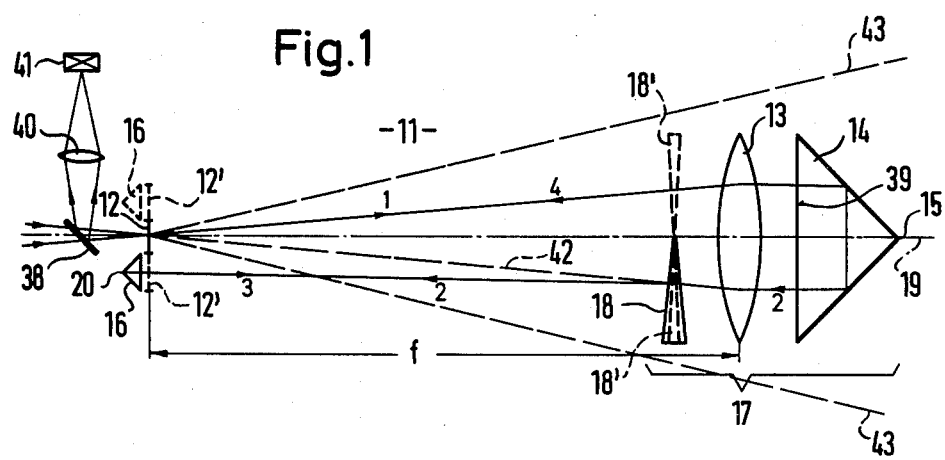
FIG. 1 is a diagrammatical plan view of a first embodiment of the invention for a fourfold passage of the beam through a measurement path.

In FIGS. 1, 3, 4, 5, 6 and 7 the line 12 provided with small cross-lines represents the cross-section of a slit which is illuminated from the left. The longitudinal direction of the slit thus extends at right angles to the plane of the drawing. Instead of the illuminated slit 12 it would also be possible to use the coil of a lamp or a laser light source, so that in order to simplify the description given below the slit 12 will simply be referred to as a light source, without the scope of application of the invention being thereby restricted.

The path of the illuminating beam for the slit 12 will first be explained with reference to FIG. 9.

The coil of an incandescent lamp 26 is imaged by way of a condenser system 27 into a lens 28 which is disposed directly behind the opening of a rotating chopper disc 29. The chopper disc 29 serves to obtain at the electrical output of the apparatus an alternating signal which is more easily processed.

The lens 28 is situated at the focal point of an achromat 30, which thus transmits a parallel light beam from the left to the slit 12.

Directly behind the lens 28 the light beam is divided by a deviating mirror 31, which projects laterally into it, into a measuring beam 32 passing straight through and a laterally deflected reference beam 33. The reference beam 33 is deflected upwards to another deviating mirror 34, by which it is again deflected substantially into the same direction as the measuring beam 32. Behind the mirrors 31 and 34 is disposed a segmental disc 35 which is rotationally fixed to the chopper disc 29 and which in the region of the measuring beam 32 and of the reference beam 33 has peripheral slits for the passage of the beams. The peripheral slits are however so shaped and offset in relation to one another that only one of the two beams 32 or 33 passes at one time through the segmental disc 35.

Figure 9:
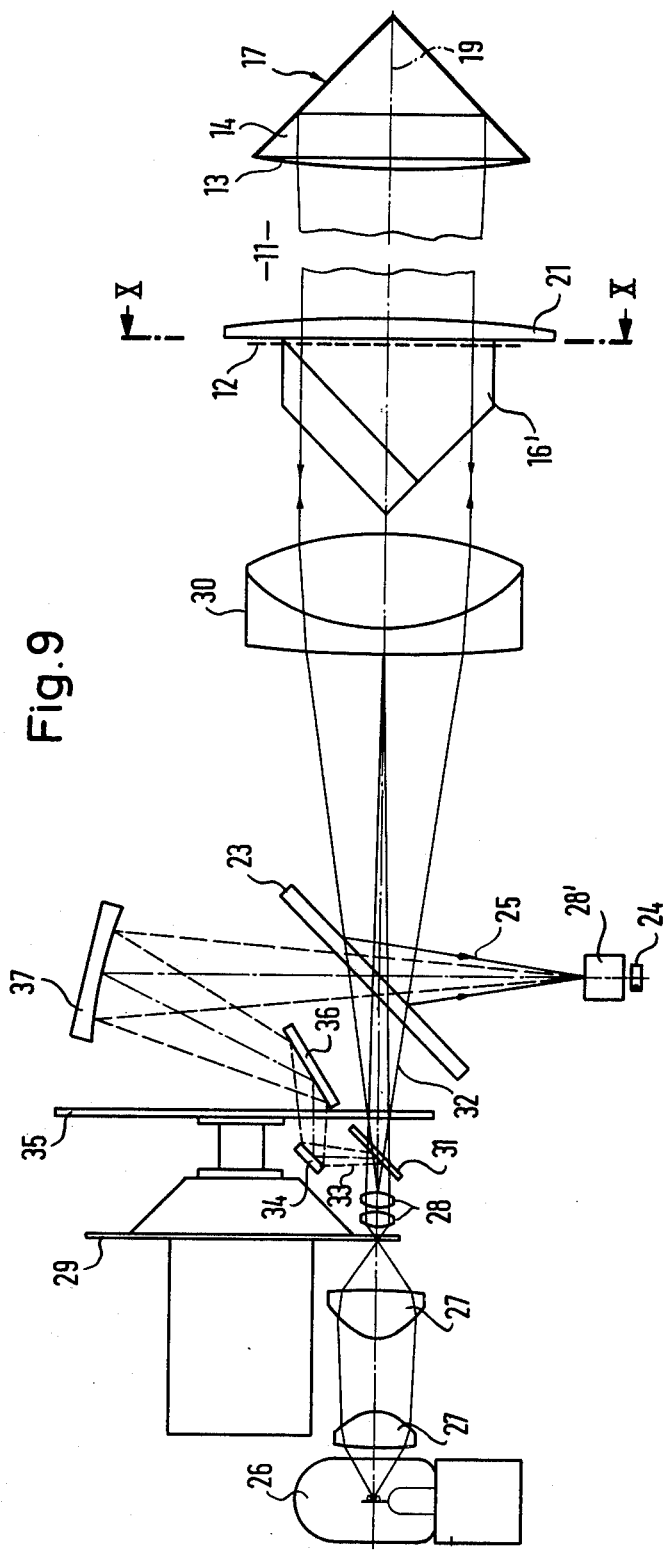
FIG. 9 is a diagrammatical side view of a transmitter-receiver apparatus which is particularly suitable for the multiple reflection arrangement of the invention, the view being taken in a direction turned 90° about the optical axis in relation to the preceding Figures.

After passing through the segmental disc 35 the measuring beam 32 passes through the slit 22 (visible in FIG. 10) of a slit mirror 23 which, as shown in FIG. 9, is disposed at an angle of 45° to the optical axis 19. The reference beam is concentrated by way of another deviating mirror 36 and a concave mirror 37, and through the aforesaid slit 22 and by way of a microlens 28', on a photoreceiver 24. The measurement beam 32 and the reference beam 33 thus pass through one and the same slit 22 in directions substantially at right angles to one another.

The measurement path 11, which is shown interrupted in FIG. 9, follows the slit 12 to the right by way of a lens 21 which will be further described below. At the end of the measurement path is situated the reflection device 17 according to the invention which throws back incident light, in a manner which will be described below, to the transmitter-receiver disposed on the left of the measurement path 11. As the result of the multiple reflection arrangement according to the invention, which will be described below, the reflected light passes in accordance with FIG. 10 at 12''''' laterally past Beck prism 16', which will likewise be described further on, onto the side parts 23a, 23b, of the slit mirror 23, whence the beam is reflected downwards to the photoreceiver 24.

Figure 10:
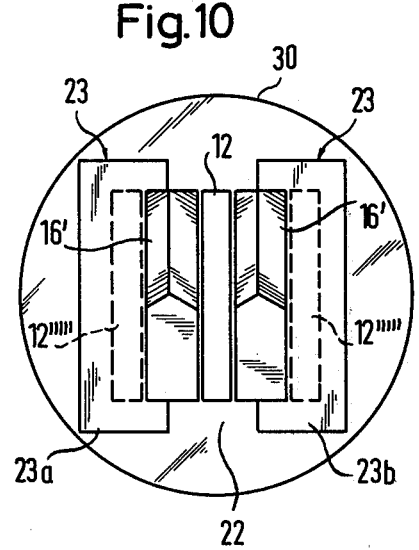
FIG. 10 is a diagrammatical view on the line X—X in FIG. 9.

The transmitter-receiver described in connection with FIGS. 9 and 10 is particularly suitable for application in the embodiment shown in FIGS. 3, 4, 5 and 7. However, FIG. 1, in which a simplified beam path with a partially transmitting mirror 38 is used, is more suitable for illustrating the basic principle of the present invention.

According to FIG. 1, the slit 12 is illuminated from the left by way of an optical system (not shown in detail) and of the partially transmitting mirror 38. At the other end of the measurement path 11 is situated the reflection device according to the invention, consisting of a retroreflecting element 14, which is more particularly in the form of a triple mirror and which has its apex 15 remote from the measurement path, a lens 13 disposed in front of the base surface 39 of the triple mirror 14, and beam deflection means in the form of an optical wedge 18. The tip of the wedge points towards the optical axis 19 and widens in the direction away from the latter. Instead of an optical wedge 18 on one side of the optical axis 19 it is also possible to dispose two wedges 18' having a smaller wedge angle, on each side of the optical axis 19, as indicated in dashed lines in FIG. 1.

Figure 8A:
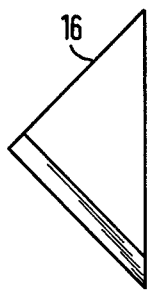
FIGS. 8a and 8b are side and rear views respectively of a Beck prism used in the multiple reflection arrangement according to the invention.
Figure 8B:

Below the light source 12 is situated a retroreflector 16 which is directly adjacent the light source 12 and whose base remote from the apex 20 has the same width and height as the light source 12. The retroreflector 16 may be made of finely divided retroreflecting material, but is preferably in the form of a Beck prism, as shown in FIGS. 8a and 8b. The illustration in FIG. 1 corresponds to a section of the Beck prism on the line I-I in FIG. 8a.

The mode of operation of the optical multiple reflection arrangement shown in FIG. 1 is as follows:

From every point of the slit or light source 12 a light beam extends through the measurement path 11 to the reflection device 17, this beam having, as indicated by dashed lines 43, a solid angle such that it overshoots the reflection device 17 on all sides to such an extent that in the event of any lateral displacement of the reflection device 17 relative to the light source 12 all regions of the reflection devcie 17 remain within the light beam. Of all the rays of this light beam which originate from the centre of the light source 12 only one individual ray 1 will be considered as an example, this ray entering the upper half of the lens 13 and there being directed parallel to the optical axis 19, because according to the invention the focal length $f$ of the lens 13 has been selected to be equal to the distance between the lens and the light source 12. The ray 1, directed parallel, enters the triple mirror 14, is offset in the latter, and passes out of the triple mirror 14 again, below the optical axis 19, parallel to its incoming direction. Because of optical laws, without the wedge 18 the reflected, offset ray 2 would pass along the dashed line 42 back to the starting point on the light source 12, that is to say, the light source 12 would be imaged in itself.

Because of the optical wedge 18 inserted in accordance with the invention, however, the reflected ray 2 is deflected in such a manner that an image 12' of it is projected directly at the side of the light source 12. Since the retroreflector 16 is situated behind the image 12' of the light source 12, the ray 2 is thrown back in itself as a reflected ray 3. On the wedge 18 the deflection effected by the latter is cancelled out and, after being again reflected and offset in the triple mirror 14, the ray 3 finally passes over into the re-reflected light beam 4, which passes to the starting point in the light source. The light now passing out through the slit 12 can be concentrated by way of the partially transmitting mirror 13 and by way of a lens 40 onto a photoreceiver 41. The boundary lines of each beam coming from the light source 12 are designated 43. As can be seen, neither a certain lateral displacement of the reflection device 17 nor a certain tipping will make any change in the imaging conditions, so that even without a rigid connection between the transmitter-receiver on the one hand and the reflection device 17 on the other hand perfect imaging and intensity conditions will exist in the receiver.

Because of the conditions of symmetry of the optical multiple reflection arrangement shown in FIG. 1, an image 12' of the light source 12 is also produced on the other side in the manner illustrated. Through the provision of another retroreflector behind this second image 12', the light impinging there can also be utilised for the measurement. The beam paths to the additional retroreflector 16 extend entirely symmetrically to the beam paths shown in the drawing, in which they are not shown simply in order not to impair the clarity of the Figure.

Figure 2:
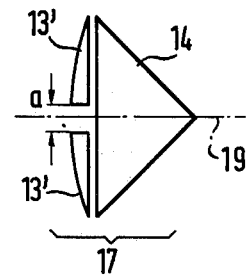
FIG. 2 shows another form of the reflection device remote from the light source, according to FIG. 1.

The wedges 18, 18', are shown in FIG. 1 only in order to illustrate the principle. In practice the offsetting of the image 12' in relation to the light source 12 is best achieved by means of two half-lenses having separate but parallel optical axes, or in accordance with FIG. 2 by dividing the lens 13 into two half-lenses spaced a distance $a$ apart. By making the distance $a$ between the optical axes adjustable, particularly in a trial arrangement, the image 12' can be brought exactly to the desired position, that is to say in particular directly adjoining the light source 12.

In an arrangement which is ready for production, however, the half-lenses 13' are cemented on the triple mirror 14 in order to avoid separate holders for these two parts.

Figure 6:
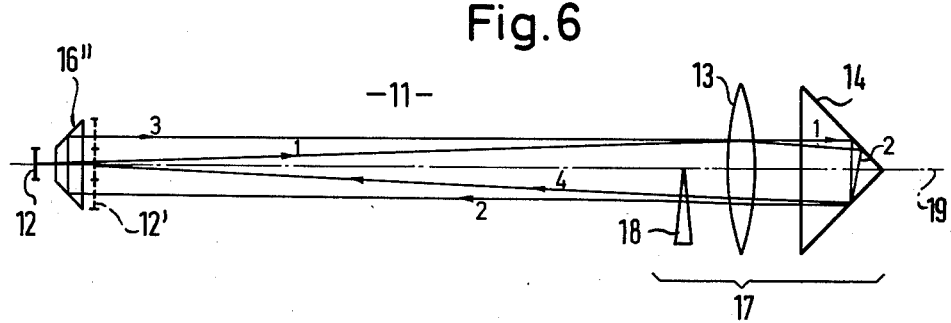
FIG. 6 is a plan view of another, simplified embodiment.

A similar arrangement to FIG. 1 is shown in FIG. 6, where however the retroreflector 16, which is preferably in the form of a Beck prism, is replaced by a flattened roof prism 16' whose flat middle portion and inclined side portions each have a width corresponding to that of the gap or light source 12, the prism 16' having the same length as the light source 12. If a flattened roof prism 16' of this kind is disposed symmetrically to the optical axis 19, as shown in FIG. 6, a light ray 1 originating from a determined point of the light source 12 passes through the measurement path 11 in the manner illustrated, merges, after refraction and reflection in the reflection device 17, into the reflected ray 2, which at the point shown enters the flattened roof prism 16" again, laterally of the light source 12, and on the symmetrically opposite side passes out as a re-reflected ray 3. Finally, after further reflection and refraction at 17 the ray 3 returns to the starting point as the ray 4 reflected for the fourth time, and then similarly to the arrangement shown in FIG. 1, is guided again to a photoreceiver by way of a partially transmitting mirror (not shown).

In comparison with that shown in FIG. 1, the arrangement shown in FIG. 6 provides the advantage that for the utilisation of the light returning on both sides of the light source 12 only a single element is necessary, namely the flattened roof prism 16". In this arrangement, as in all other embodiments, insensitivity to adjustment can also be achieved through the fact that each beam originating from the light source 12 overshoots the reflection device 17 on all sides.

Figure 7:
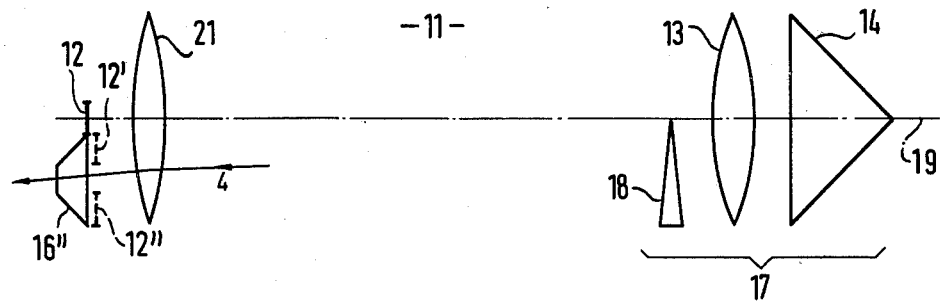
FIG. 7 is a plan view of a modification of the embodiment according to FIG. 6.

If it is not desired that the light beam finally passing out again from the multiple reflection arrangement should pass through the light source 12 itself, it is possible to use the arrangement shown in FIG. 7, in which the flattened roof prism 16" is disposed at the side of and immediately adjoining the light source 12. With the aid of the reflection device 17 of the invention the image 12' of the light source is first produced in the position shown, after being reflected once. By reflection within the flattened roof prism 16" this image is offset downwards by twice the width of the light source, to form the image 12". On renewed passage through the optical wedge 18 half of this offsetting is cancelled out, so that finally the ray 4 corresponding to the fourth passage passes out through the flattened portion of the roof prism 16" in the manner illustrated, at the side of the light source 12. As the result of this arrangement, it is not necessary to provide a partially transmitting mirror, and thus a better light yield is obtained.

The action of the lens 21, the focal length of which is equal to that of the lens 13, is explained below with reference to FIG. 4.

A particularly preferred embodiment will now be described with reference to FIG. 3. This embodiment differs from that shown in FIG. 1 particularly in that the retroreflector 16' is relatively twice as wide and that the deflection of the beam by means of the wedge 18 is only so great that the image 12' after the first reflection lies directly on one half of the retroreflector 16'. By reflection within the retroreflector 16' the image 12' is shifted to the position 12" in the lower half. The beam 3 now returning to the reflection device 17 is refracted in the wedge 18 in such a manner that the offsetting is cancelled by one light source width and the re-reflected beam 4 re-enters the upper portion of the retroreflector 16'. An image 12''' of the light source is thus again formed at the position of the image 12'. The image 12'''' is again displaced by the retroreflector 16' into the lower half, to the position 12''''. Since the returning beam 5 now entering the upper half of the reflection device 17 is finally again deflected downwards at the wedge 18 in the form of a reflected beam 6, the beam 6 passes out of the arrangement, past the retroreflector 16'. Thus directly at the side of the retroreflector 16' a fifth image 12''''' of the light source 12 is thus formed.

As the result of the symmetry conditions another retroreflector 16' can also be disposed on the other side of the light source 12. A fifth image 12''''' on the outer side of this retroreflector 16' and a corresponding exit beam from the device would then also be obtained.

Figure 3:
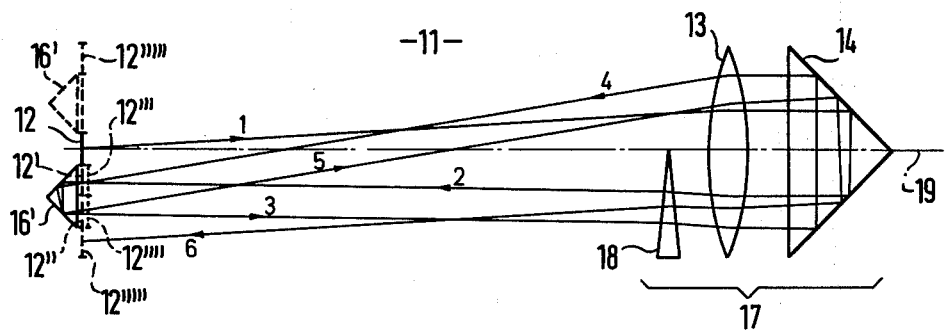
FIG. 3 is a diagrammatical plan view of another form of a multiple reflection arrangement according to the invention for six passages of the beam.
Figure 4:
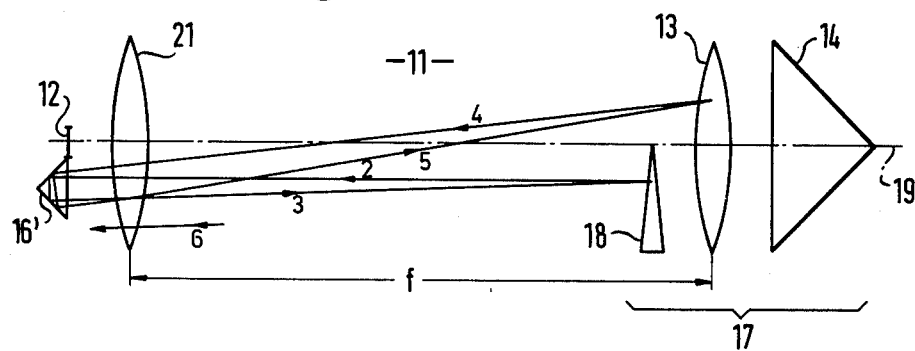
FIG. 4 is a modification of the embodiment shown in FIG. 3.

In order to ensure in a multiple reflection arrangement according to FIG. 3 that beams passing out of one half of the reflection device 17 will re-enter this half after reflection on the transmitter-receiver side, in the particularly preferred embodiment shown in FIG. 4 a lens 21 is disposed in front of the light source in the manner illustrated, the focal length of this lens being equal to the distance from the reflection device 17 and thus equal to the focal length of the lens 13. The mode of operation of the lens 21 is illustrated by the beams 3 and 5 in FIG. 4. Whereas in the embodiment shown in FIG. 3 the reflected beams 3 and 5 extend parallel to the beams 2 and 4 respectively (so that the danger exists that these beams may possibly no longer enter the reflection device 17 or the correct half of the reflection device 17), the lens 21 ensures that the beams 3, 5, will return to the same point of the reflection device 17 from which the respective beam 2 or 4 originated. The same also applies to all other beams passing out of the reflection device 17 and then retroreflected at 16'. For graphic reasons the measurement path 11 in all embodiments is shown far too short in relation to the distance between the optical elements of the reflection device 17 and to the distance between the reflectors 16', 16" and the lens 21. In practice the distance between the optical elements on one side of the measurement path in relation to the length of the latter can be neglected.

In FIG. 4 the lens 21 is shown so large that it even projects latterally beyond the outgoing beam 6. However, it need extend only to the edge of the retroreflectors 16', so that the exit beams 6 pass by the lens 21. A construction of the lens 21 of this kind is used in the embodiment which will be described below and which is illustrated in FIG. 5.

Figure 7A:
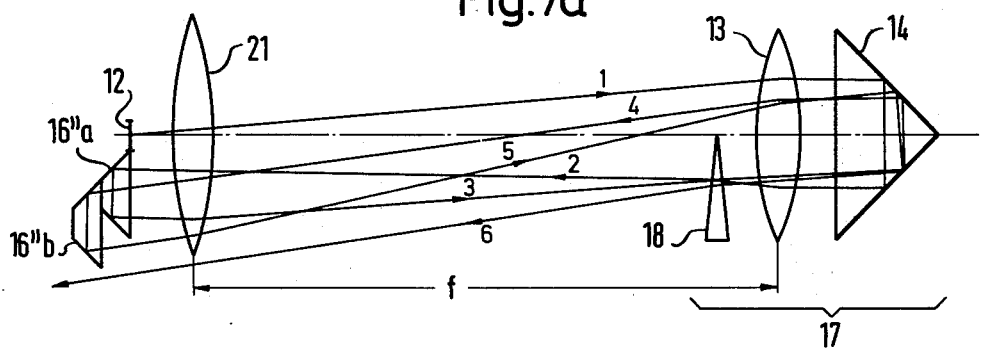
FIG. 7a is a further development of the embodiment shown in FIG. 7.

The function and construction of the lens 21 according to FIG. 7 are the same as described above in connection with FIG. 4. This is also illustrated in detail in the embodiment shown in FIG. 7a, where in addition the first roof prism 16"a is supplemented by a second, identical roof prism 16"b mounted on it and offset downwards by one light source width. The number of passages of the beam is thereby increased by 2. A further increase can be achieved according to the invention by correspondingly adding further prims 16"c, d, and so forth.

Figure 5:
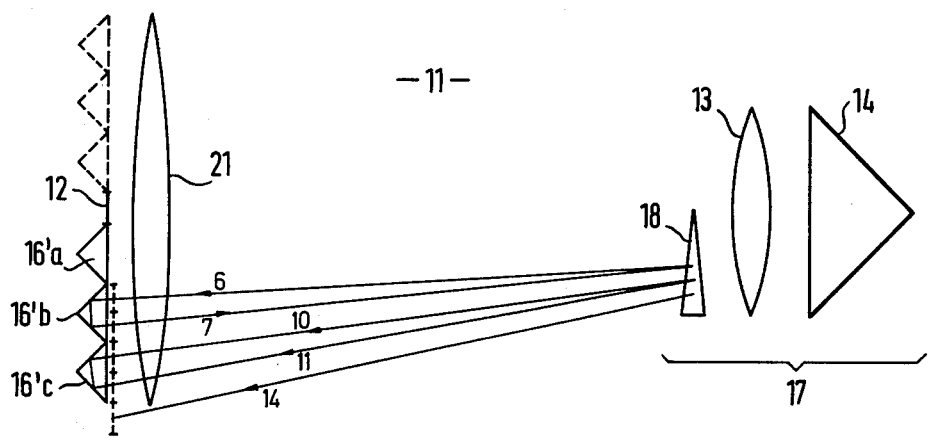
FIG. 5 is a diagrammatical plan view of another form of the multiple reflection arrangement according to the invention for a total of fourteen passages of the beam through the measurement path.

While the embodiment shown in FIG. 4 permits a sixfold passage of the light beam through the measurement path 11, a substantially larger number of passages can be achieved by aligning additional retroreflectors 16'a, 16'b, 16'c, etc., as shown in FIG. 5. Each additional retroreflector provides four additional passages, so that in the embodiment shown in FIG. 5 the light beam passes laterally out of the device only after fourteen passages. Particularly in embodiments having a plurality of juxtaposed retroreflectors 16' the lens 21 is of special importance for the purpose of effectively uncoupling the two halves of the reflection device 17.

In the embodiments shown in FIGS. 3 to 5, the Beck prisms shown in FIGS. 8a and 8b are particularly suitable as retroreflectors 16', because their base area can without difficulty be made equal to the area of the slit and they can be disposed close side by side as shown in FIG. 5. This can be seen particularly clearly in FIG. 10, where the Beck prisms 16' are shown directly at the side of the slit 12. Here it can be seen particularly clearly that the base surface of the Beck prisms should be selected to be twice as wide as the width of the slit, while the length of the base is equal to that of the slit. FIG. 10 also shows particularly clearly the good light yield which can be achieved with a multiple reflection arrangement according to the invention. The entire light intensity passes through the slit 22 of the slit mirror 23 to the slit 12. Since the slit images 12''''' appear at the side of the Beck prisms 16', the entire light intensity of the measuring beams finally passing out of the multiple reflection arrangement also passes completely to the side portions 23a, 23b, of the slit mirror 23. From these side portions they are concentrated by the fully reflecting mirror surfaces onto the photoreceiver 24 (FIG. 9).

Because of the rotation of the chopper disc 29 and of the segmental disc 35, not only is alternating light transmitted to the photocell 24, but in addition at any one moment of time only either light 25 reflected from the measurement path 11 or reference light 33 impinges on the photoreceiver 14. By comparison of the two signals in a suitable electronic evaluation unit it is thus always possible to determine the light intensity of the light beams returning from the measurement path 11 in relation to the reference beam 33. Electronic evaluation circuit arrangement of this kind are known per se for the comparison of two light beams.

What we claim is:

1. An optical multiple-reflection arrangement having first and second reflection devices at respective ends of a measurement path and having a light source at one end of the measurement path, the light source and the reflection devices being so constructed and arranged that a light beam starting from the light source passes at least four times through the measurement path before it passes out of the latter, the first reflection device disposed at the end of the measurement path removed from the light source comprising a lens having a focal length equal to its distance from the light source, behind this lens a first retroreflecting element which reflects an incoming light beam in the same direction but offset laterally, and light beam deflection means which impart to at least one of the incoming and outgoing beams of the retroreflecting element a deflection such that the image made of the light source by the reflection device lies at the side of the light source; the second reflection device being a second retroreflector disposed near, and outside the plane of the image made of the light source by the first reflection device.

2. An arrangement according to claim 1, wherein the beam deflection means comprises an optical wedge occupying one half of the beam path.

3. An arrangement according to claim 1, wherein the beam deflection means comprises two optical wedges disposed on one and the other side respectively of the beam path.

4. An arrangement according to claim 1, wherein the beam deflection means are formed by two part-lenses whose optical axes are offset in relation to one another.

5. An arrangement according to claim 1, wherein the beam deflection means are formed by grinding one half of the said lens or of the first retroreflecting element so as to obtain a deviation from the normal shape.

6. An arrangement according to claim 4, wherein the half-lenses are plano convex and have their plane surface cemented on the likewise plane inlet surface of the first retroreflecting element.

7. An arrangement according to claim 4, wherein the offset distance between the half-lenses is variable.

8. An arrangement according to claim 1, wherein the first retroreflecting element is a triple mirror.

9. An arrangement according to claim 1, wherein the first reflection device projects the image of the light source so that said image directly adjoins the light source.

10. An arrangement according to claim 1, wherein the second retroreflector forming the second reflection device effects only a reversal of the beam without offsetting it.

11. An arrangement according to claim 10, wherein the second retroreflector consists of finely divided retroreflecting material.

12. An arrangement according to claim 10, wherein the second retroreflector is a roof prism whose roof edge is situated in the middle of the image of the light source.

13. An arrangement according to claim 10, wherein the second retroreflector is a single triple mirror whose apex is situated in the middle of the image of the light source.

14. An arrangement according to claim 10, wherein the second retroreflector is a Beck prism whose apex is situated in the middle of the image of the light source.

15. An arrangement according to claim 12, wherein the base of the prism is equal in size to the image of the light source.

16. An arrangement according to claim 1, wherein the second retroreflector forming the second reflection device effects a reversal of the beam with lateral offsetting by at least the size of the image of the light source.

17. An arrangement according to claim 16, wherein the lateral offsetting corresponds exactly to the size of the light source.

18. An arrangement according to claim 16, wherein the second retroreflector is a roof prism onto whose half facing the light source the image of the light source is projected.

19. An arrangement according to claim 16, wherein the second retroreflector is an arrangement of a plurality of triple mirrors, the image of the light source being projected onto the half facing the light source.

20. An arrangement according to claim 16, wherein the second retroreflector is a Beck prism onto whose half facing the light source the image of the light source is projected.

21. An arrangement according to claim 16, wherein the second retroreflector directly adjoins the light source.

22. An arrangement according to claim 16, wherein the base of the second retroreflector is twice as wide as the image of the light source.

23. An arrangement according to claim 16, wherein in front of the second retroreflector there is disposed on the optical axis another lens whose focal length is equal to the distance thereof from the first reflection device.

24. An arrangement according to claim 23, wherein a plurality of retroreflectors are disposed directly side by side next to said second retroreflector.

25. An arrangement according to claim 1, wherein two said second retroreflectors are disposed in identical arrangements symmetricaly on both sides of the light source.

26. An arrangement according to claim 16, wherein the lateral offsetting in the direction of the light source amounts to twice the size of the light source.

27. An arrangement according to claim 26, wherein said second retroreflector is a flattened roof prism.

28. An arrangement according to claim 27, wherein the flattened middle portion and the two lateral inclined portions of the roof prism are equal in size to the light source and the centre of the roof prism lies on the optical axis.

29. An arrangement according to claim 1, wherein the light source is an illuminated slit.

30. An arrangement according to claim 29, wherein a Beck prism is disposed on at least one side of the slit, adjoining the latter.

31. An arrangement according to claim 30, wherein the slit is illuminated by the slit of an inclined slit mirror, and the side portions of the slit mirror receive the light reflected past the at least one Beck prism and guide it onto a photoreceiver.

32. An arrangement according to claim 31, wherein in alternation with the light from the measurement path a reference light beam from the same main light source is also guided through the slit of the inclined slit mirror onto the photoreceiver.

33. An arrangement according to claim 3 wherein the wedges are directed with their apex towards the main axis.

34. An arrangement according to claim 3 wherein the wedges have their apex facing away from the main axis in such a manner that the light beam deflected by the wedges intersects the main axis.

35. An arrangement according to claim 1, wherein said second retroreflector is disposed in front of the image made of the light source by said first reflection device.

36. An arrangement according to claim 1, wherein said second retroreflector is disposed behind the image made of the light source by said first reflection device.

37. An arrangement according to claim 10, wherein said second retroreflector is a triple bar.

38. An arrangement according to claim 13, wherein the base of the triple mirror is equal in size to the image of the light source.

39. An arrangement according to claim 16, wherein said second retroreflector is a triple mirror, the image of the light source being projected onto the half facing the light source.

40. An arrangement according to claim 2, wherein the wedge is directed with its apex towards the main axis.

41. An arrangement according to claim 2, wherein the wedge has its apex facing away from the main axis so that the light beam deflected by the wedge intersects the main axis.

* * * * *